United States Patent
Klewer et al.

(10) Patent No.: US 10,052,048 B2
(45) Date of Patent: Aug. 21, 2018

(54) RESPIRATORY MONITORS AND MONITORING METHODS

(75) Inventors: Jasper Klewer, Utrecht (NL); Haris Duric, Helmond (NL); Teunis Jan Ikkink, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1018 days.

(21) Appl. No.: 12/989,484

(22) PCT Filed: May 4, 2009

(86) PCT No.: PCT/IB2009/051823
§ 371 (c)(1),
(2), (4) Date: Oct. 25, 2010

(87) PCT Pub. No.: WO2009/138896
PCT Pub. Date: Nov. 19, 2009

(65) Prior Publication Data
US 2011/0046499 A1    Feb. 24, 2011

Related U.S. Application Data

(60) Provisional application No. 61/053,186, filed on May 14, 2008.

(51) Int. Cl.
*A61B 5/08*    (2006.01)
*A61B 5/113*    (2006.01)
(Continued)

(52) U.S. Cl.
CPC ............ *A61B 5/113* (2013.01); *A61B 5/0816* (2013.01); *A61B 7/003* (2013.01); *H04B 17/0085* (2013.01); *A61B 2562/0219* (2013.01)

(58) Field of Classification Search
CPC ....... A61B 7/003; A61B 5/113; A61B 5/0816; A61B 2562/0219; H04B 17/0085
(Continued)

(56) References Cited

U.S. PATENT DOCUMENTS 5,309,922 A    5/1994    Schechter et al.
6,997,882 B1 *    2/2006    Parker et al. ................. 600/534
(Continued)

FOREIGN PATENT DOCUMENTS

EP        0 956 820 A    11/1999
JP        2004187961 A    7/2004
(Continued)

*Primary Examiner* — Tiffany Weston

(57) ABSTRACT

A respiratory monitor comprises: a first sensor (20, 70) configured to generate a respiration-related motion monitoring signal (72) indicative of respiration related motion; a second sensor (20, 22, 80, 82) configured to generate a sound monitoring signal (84) indicative of respiration-related sound; and a signals synthesizer (90) configured to synthesize a respiratory monitor signal (46) based on the respiration-related motion monitoring signal and the respiration-related sound monitoring signal. A sensor for use in respiratory monitoring comprises an accelerometer (30) and a magnetometer (32) together defining a unitary sensor (20) configured for attachment to a respiring subject (10) so as to move as a unit responsive to respiration related motion of the respiring subject.

11 Claims, 2 Drawing Sheets

Figure 1:
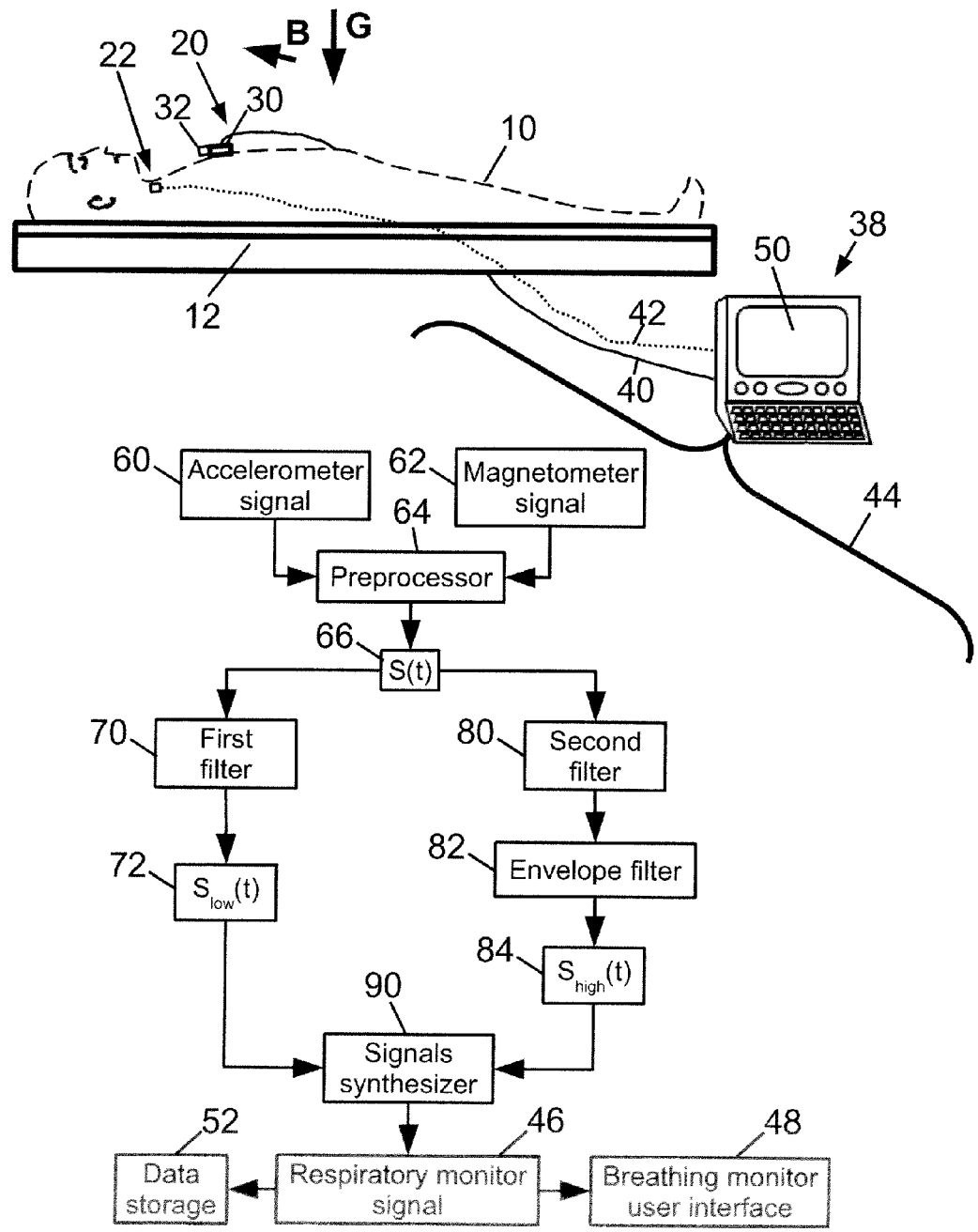

(51) Int. Cl.
*A61B 7/00* (2006.01)
*H04B 17/00* (2015.01)

(58) Field of Classification Search
USPC .................................................. 600/529–534
See application file for complete search history.

(56) References Cited

U.S. PATENT DOCUMENTS

| | | | |
|---|---|---|---|
| 7,423,537 | B2 | 9/2008 | Bonnet et al. |
| 7,602,301 | B1 * | 10/2009 | Stirling et al. ............. 340/573.1 |
| 7,857,772 | B2 | 12/2010 | Bouvier et al. |
| 8,162,857 | B2 | 4/2012 | Lanfermann et al. |
| 8,862,422 | B2 | 10/2014 | Ikkink et al. |
| 2005/0027216 | A1 * | 2/2005 | Guillemaud et al. ......... 600/595 |
| 2006/0074334 | A1 * | 4/2006 | Coyle ........................... 600/529 |
| 2007/0118054 | A1 | 5/2007 | Pinhas et al. |
| 2007/0270665 | A1 | 11/2007 | Yang et al. |
| 2008/0082018 | A1 * | 4/2008 | Sackner et al. ............... 600/538 |

FOREIGN PATENT DOCUMENTS

| | | | | |
|---|---|---|---|---|
| WO | WO 92/09232 | A1 | 6/1992 | |
| WO | WO 03/005893 | A2 | 1/2003 | |
| WO | WO 2006/038074 | A1 | 4/2006 | |
| WO | 2006124768 | A1 | 11/2006 | |
| WO | WO 2006/117731 | A1 | 11/2006 | |
| WO | WO 2006/126117 | A2 | 11/2006 | |
| WO | WO 2007/088539 | * | 8/2007 | ............. A61B 5/113 |
| WO | WO 2008/007261 | * | 1/2008 | |

* cited by examiner

RESPIRATORY MONITORS AND MONITORING METHODS

CROSS REFERENCE TO RELATED APPLICATIONS

This application claims the benefit of U.S. provisional application Ser. No. 61/053,186 filed May 14, 2008, which is incorporated herein by reference.

The following relates to the medical arts, information arts, and related arts. It finds application in respiratory monitoring of patients, laboratory subjects, and the like.

Respiration is an important physiological process, and respiratory monitoring has numerous applications, such as: early detection of worsening patient condition; providing a respiratory gating signal for medical imaging or other medical procedures, tests, or the like that are sensitive to respiration; detecting when a subject is awake or asleep; immediate detection of respiratory failure; and so forth.

Some respiratory monitors and monitoring methods employ an accelerometer to detect chest motion. The accelerometer detects chest motion indirectly, by measuring deviation of the sensor orientation respective to the earth's gravitational field caused by the chest motion. As a result, for some positions of the subject the accelerometer may detect the chest motion only weakly or not at all. Such sensors are also susceptible to artifacts due to subject motions unrelated to respiration.

Other respiratory monitors and monitoring methods employ a piezoelectric sensor to detect respiratory sound. A problem with these sensors is that they have low sensitivity to shallow breathing, for which sound generation is low.

The following provides a new and improved respiratory monitors and monitoring methods which overcome the above-referenced problems and others.

In accordance with one disclosed aspect, a respiratory monitor is disclosed, comprising: a first sensor configured to generate a respiration-related motion monitoring signal indicative of respiration-related motion; a second sensor configured to generate a sound monitoring signal indicative of respiration-related sound; and a signals synthesizer configured to synthesize a respiratory monitor signal based on the respiration-related motion monitoring signal and the respiration-related sound monitoring signal.

In accordance with another disclosed aspect, a respiratory monitoring method is disclosed, comprising: acquiring a respiration-related motion monitoring signal indicative of respiration-related motion of a respiring subject; acquiring a sound monitoring signal indicative of respiration-related sound generated by the respiring subject; and synthesizing a respiratory monitor signal based on the respiration-related motion monitoring signal and the respiration-related sound monitoring signal.

In accordance with another disclosed aspect, a sensor for use in respiratory monitoring is disclosed, comprising an accelerometer and a magnetometer together defining a unitary sensor configured for attachment to a respiring subject so as to move as a unit responsive to respiration-related motion of the respiring subject.

One advantage resides in providing respiratory monitoring methods and respiratory monitors with improved robustness against motion or varied positioning of the monitored subject.

Another advantage resides in providing respiratory monitoring methods and respiratory monitors with improved monitoring of different respiratory modes.

Further advantages of the present invention will be appreciated to those of ordinary skill in the art upon reading and understand the following detailed description.

FIG. 1 diagrammatically shows a subject being monitored by a respiratory monitor.

Figure 2:
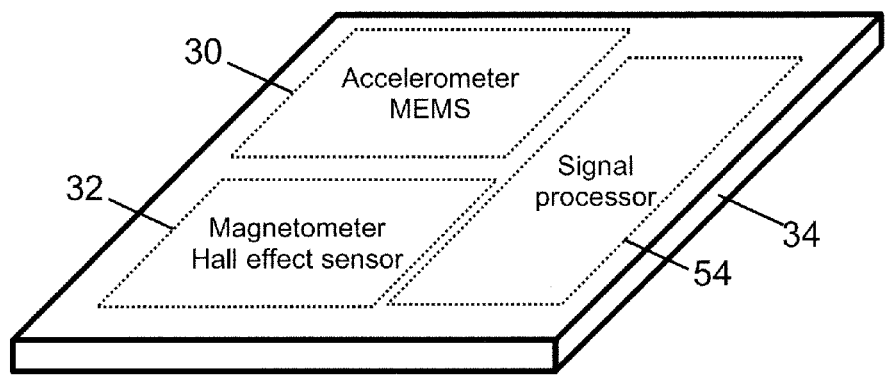

FIG. 2 diagrammatically shows an embodiment of a monolithically integrated accelerometer and magnetometer configured for use in a respiratory monitor.

Figure 3:
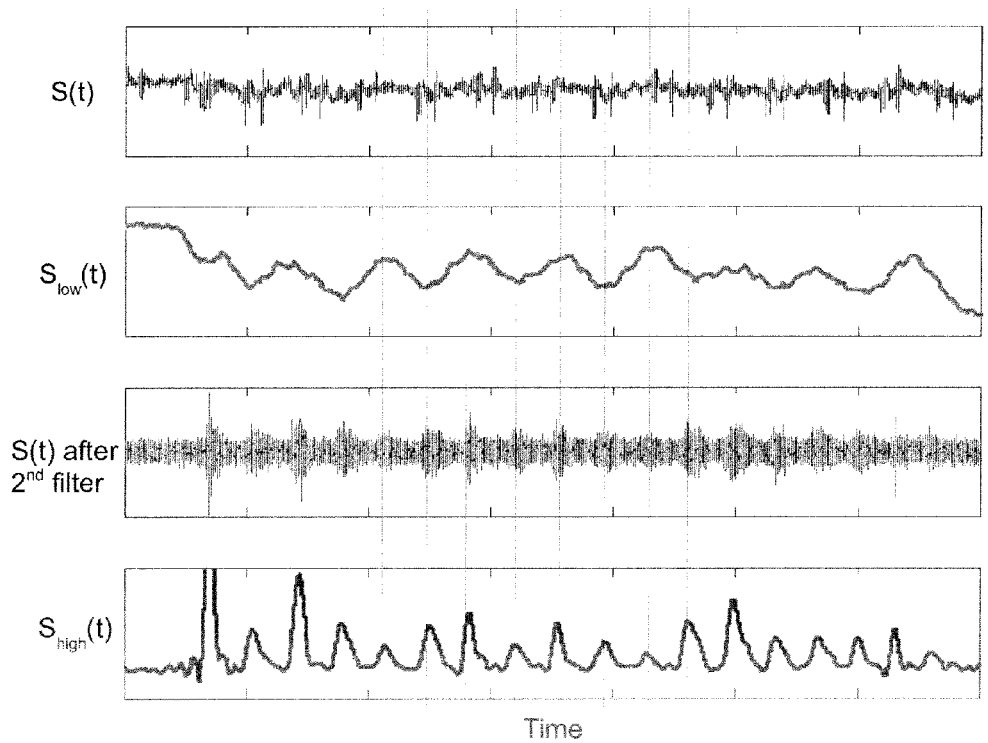

FIG. 3 diagrammatically shows plots as a function of time of selected signals generated by respiratory monitoring processing performed by the respiratory monitor of FIG. 1.

With reference to FIG. 1, a subject 10 lies on a support 12. The illustrated subject 10 is a human subject; however, animal subjects are also contemplated. The support 12 is a table or other generally flat surface on which the subject 10 lies; however, other supports such as a chair are also contemplated, and moreover the subject may be standing, floating in water, or otherwise not residing in a support.

The subject 10 is monitored by a sensor 20 that outputs a sensor signal indicative of at least respiration-related motion, such as chest motion accompanying inhalation and exhalation. Optionally, the sensor signal output by the sensor 20 may also be indicative of respiration-related sound, such as sound generated by respiration-related turbulent airflow in the upper airways. In other embodiments, respiration-related sound is not monitored, or is monitored by an optional separate sensor 22.

As an illustrative example, in some embodiments the sensor 20 includes at least one sensor selected from a group consisting of an accelerometer, a gyroscope, a tilt sensor, or a magnetometer, and the optional additional sensor 22 includes at least one sensor selected from a group consisting of an accelerometer, a microphone, a hydrophone, a piezoelectric transducer, and a vibration transducer. Some sensors, such as accelerometers, provide sensitivity to both respiration-related motion and respiration-related sound. For a sensor intended to detect of respiration-related sound, it is advantageous to have the sensor located on or near the throat of the subject 10, as in the case of illustrated sensor 22, although a chest-mounted sensor may also be suitable. For a sensor intended to detect respiration-related motion, a location on the chest, throat, or other region that moves with the respiratory cycle is advantageous.

With continuing reference to FIG. 1 and with brief reference to FIG. 2, one advantageous embodiment of the sensor 20 is an accelerometer 30 and a magnetometer 32 together defining the unitary sensor 20 configured for attachment to the respiring subject 10 so as to move as a unit responsive to respiration-related motion of the respiring subject 10. The attachment may be via an adhesive or glue, via a strip of adhesive tape holding the sensor 20 to the subject 10, via a strap wrapped around the chest of the subject 10, or so forth. As diagrammatically illustrated in FIG. 2, such a sensor can be constructed by monolithically integrating the accelerometer 30 and the magnetometer 32 on a common substrate. In one suitable embodiment, the accelerometer 30 and the magnetometer 32 are both fabricated on a common silicon substrate 34, with the accelerometer 30 being embodied by a microelectromechanical system (MEMS) and the magnetometer 32 being embodied as a Hall effect sensor. By being both fabricated on the common substrate 34, the accelerometer 30 and the magnetometer 32 move together as a unit responsive to respiration-related motion, and also vibrate together as a unit responsive to respiration-related sound.

The advantage of employing the combination of the accelerometer 30 and the magnetometer 32 as the sensor 20 is due to the directional dependence of each sensor alone. The accelerometer 30 detects the gravitational acceleration G, and respiration-related motion is detected because it generally causes change in the orientation of the accelerometer 30 respective to the gravitational acceleration vector G. The accelerometer 30 measures gravity G as a constant acceleration G, which however depends on the angle ($\varphi$) of the accelerometer 30 with respect to the angle of the gravity vector G according to the relationship $A=G \cdot \cos(\varphi)$ where A is the acceleration measured by the accelerometer 30 and G is the magnitude of the gravitation vector G. Respiration-related motion, such as chest motions due to breathing, cause a slow and generally periodic change of orientation $\varphi$ of the accelerometer 30. This results in a slowly changing measured acceleration A.

However, depending upon the position of the subject 10 and the location of attachment of the sensor 20 on the subject 10, it is possible that the respiration-related motion may be in a direction that does not cause a change in the orientation $\varphi$ of the accelerometer 30, or may be in a direction that causes only a small change in the orientation $\varphi$ of the accelerometer 30. In such cases, the accelerometer 30 will have no sensitivity, or little sensitivity, to the respiration-related motion.

Further inclusion of the magnetometer 32 enables this directionality of the accelerometer 30 to be compensated. The magnetometer 32 is sensitive to the orientation of the magnetometer 32 (or, more generally, the orientation of the unitary sensor 20) respective to the earth's magnetic field vector B. The direction of the earth's magnetic field vector B varies with location on the surface of the earth, but is always generally transverse to the gravitational vector G (except possibly near the north or south magnetic pole). Suitable processing of the accelerometer signal output by the accelerometer 30 and the magnetometer signal output by the magnetometer 32 enables generation of a sensor signal indicative of respiration-related motion that is operative regardless of the orientation of the unitary sensor 20.

With continuing reference to FIGS. 1 and 2, the respiration monitor further includes one or more processing components configured to receive signals from the one or more sensors 20, 22 and to compute a respiratory monitor signal therefrom. In the embodiment of FIG. 1, such one or more processing components are embodied as a computer 38 operatively connected with the one or more sensors 20, 22 by respective wires or cables 40, 42. Alternatively, a wireless connection is also contemplated, such as a radio frequency link or an infrared link. The computer 38 includes a processor, memory such as random access memory (RAM), magnetic storage, optical storage, or the like, and software executable by the processor (memory, storage, and processor components not individually shown) configured to embody a respiratory monitoring process 44 that converts the sensor signal or signals received from the one or more sensors 20, 22 into a respiratory monitor signal 46 that can be output via a breathing monitor user interface 48 (such as a display 50 of the computer 38), stored in a data storage 52 (such as a magnetic or optical storage medium of the computer 38), or otherwise utilized. FIG. 1 shows the entire processing method 44 embodied by the computer 38. Additionally or alternatively, some or all of the processing may be embodied by a signal processor 54 embodied as circuitry formed on the substrate 34 together with the accelerometer 20 and magnetometer 22, as shown in FIG. 2, or may be otherwise embodied, for example as a dedicated respiratory monitor readout unit (not shown), or as a dedicated multi-purpose patient monitor (not shown).

With reference to FIG. 1, the illustrative respiratory monitoring process 44 receives as inputs an accelerometer signal 60 and a magnetometer signal 62 from the magnetometer 32. A preprocessor 64 or other signal processor generates a sensor signal S(t) 66 based on the accelerometer signal 60 output by the accelerometer 30 and the magnetometer signal 62 output by the magnetometer 32. Some suitable approaches for generating the sensor signal S(t) 66 are described in the following.

The orientation ro attitude of the unitary sensor 20 has three degrees of freedom (DOF) with respect to a reference frame defined by the directions of gravity vector G and earth magnetic field vector B. DOF orientation of the sensor 20 can be represented with respect to an earth-fixed reference coordinate frame. To this end the sensor 20 can be viewed as a body-fixed coordinate frame, having three orthogonal axes. The sensor 20 is said to have assumed the reference attitude if the x, y, and z-axes of the body-coordinate frame are lined-up to the corresponding axes of the reference coordinate frame defined by the vectors G, B.

One suitable processing approach is based on the recognition that any three-DOF attitude can be viewed as the result of three successive rotations about perpendicular axes. The corresponding three angles are known as Euler angles, and are defined respective to axes which can be can be either body-fixed or earth-fixed and arranged in different orders (rotation is a non-commutative operation; in other words, the order in which successive rotations are carried out affects the final orientation). One known Euler angle convention, commonly used in aviation, is roll-pitch-yaw. The corresponding axes are body-fixed with the roll axis being the nose-tail axis of the airplane, the pitch axis running from wingtip to wingtip, and the yaw axis running from top to bottom.

Another suitable processing approach is based on the attitude matrix, which is also called the rotation matrix or direction cosine matrix. This is a 3×3 matrix in which each of the respective columns gives the direction of the corresponding base vector of the body-coordinate system in terms of the reference coordinate system. The matrix representation is convenient for calculations. The matrix corresponding to a second attitude that is achieved by rotating the body from a first attitude can be described by a multiplication of the first attitude matrix by a rotation matrix.

Another suitable processing approach is the axis-angle approach. Here, any attitude is considered to be the result of a single rotation (starting from the reference attitude) about a certain axis and through a certain angle. The direction of the rotation axis covers two of the three degrees of freedom, while the rotation angle is the third.

Another suitable processing approach is the quaternion approach, which has only one degree of redundancy. As a result, the quaternion approach is readily rescaled to represent a pure rotation.

The orientation change of the sensor 20 resulting from respiration-related motion can be considered as a small rotation back and forth about a selected axis. The rotation angle is typically a few degrees or less. The direction of the rotation axis is generally not known a priori. The processing of the signals 60, 62 determines the attitude of the unitary sensor 20 as a function of time, and the orientation change due to respiration can be calculated from the instantaneous attitude and a time-averaged version of the attitude, according to the relationship $^r\Delta C \cdot ^r\hat{C} = ^rC \Rightarrow ^r\Delta C = ^rC \cdot ^r\hat{C}^T$ where $^rC$ is the instantaneous attitude matrix (the superscript $^r$ indicates that it is expressed in terms of the reference coordinate frame), $^r\hat{C}$ is the matrix of time-averaged attitude, and $^r\Delta C$ is the orientation change due to respiration-related motion. The superscript $^T$ denotes the transpose operator, which for unitary matrices (a class that includes rotation matrices) is identical to the inverse operator. The matrix of time-averaged attitude is not a time-average of the attitude matrix. Time-averaging of the coefficients of the attitude matrix leads to a matrix that is not a pure rotation matrix anymore. A rotation matrix is a unitary matrix, meaning that its columns have unity length and are mutually orthogonal (this leads to six degrees of redundancy).

To establish the matrix of time-averaged attitude, the time average of the attitude matrix is orthogonalized. In one embodiment a standard numerical procedure such as Gram-Schmidt orthonormalization is used. Another approach for obtaining a matrix of time-averaged attitude is to iteratively optimise a rotation matrix (by applying successive corrective rotations to it) such that it matches the time-average of the attitude matrix with a minimal or reduced value of a suitable error criterion, such as the rms vector difference taken across the three columns. In another approach for obtaining a matrix of time-averaged attitude, the magnetic and gravity field vectors B, G are time-averaged, and the time-averaged attitude is determined from the time-averaged field vectors. This approach is similar to how instantaneous attitude is determined from the instantaneous field vectors, see for example WO/2006117731 A1.

Yet another illustrative approach is suitably employed in conjunction with the quaternion representation. Since a quaternion has only one degree of redundancy, the transition from time-averaged quaternion coefficients to a quaternion of time-averaged attitude is straightforward. The degree of redundancy is expressed by the condition that the rms sum of the four quaternion coefficients (that is, the quaternion length) be unity. Hence the quaternion of time-averaged attitude $\hat{q}$ can be found by dividing the time-averaged quaternion $\bar{q}$ by its length:

$$\hat{q} = \frac{\bar{q}}{\|\bar{q}\|}. \quad (1)$$

The quaternion $\Delta q$ corresponding to the orientation change due to respiration-related motion is found from:

$$\Delta q \otimes \hat{q} = q \Rightarrow \Delta q = q \otimes \hat{q}^*, \quad (2)$$

where q is the quaternion representing the instantaneous attitude, $\otimes$ is the quaternion product operator and * is the conjugation operator (which for a unity length quaternion may replace the inverse operator).

These approaches address obtaining the orientation change due to respiration-related motion. This orientation change is a 3 DOF rotation. For respiration detection it is desirable to have a single signal, such as the sensor signal S(t) 66, that gives the instantaneous rotation angle due to respiration-related motion. The rotation axis of the orientation change is of less importance. Obtaining the rotation angle formally involves converting the orientation change from the matrix or quaternion representation to the axis-angle representation. However since the orientation change is relatively small (typically a few degrees or less), one can take the rms sum of the last three quaternion components (which equals the sine of half the rotation angle). A property of the quaternion representation is that any quaternion q and its complement –q (negation of the coefficients) represent the same rotation. This may result in discontinuities of the quaternion across successive sampling instants. To avoid these discontinuities, one can change the sign of the quaternion as appropriate, that is, take –$\Delta q$ if the first component of the quaternion $\Delta q$ is negative; take $\Delta q$ otherwise. The signal thus obtained is representative of the instantaneous rotation angle of the sensor 20 with respect to its average orientation. A more or less periodic angle as a function of time is expected for respiration-related motion.

With continuing reference to FIG. 1, for the illustrative sensor 20 including accelerometer and magnetometer components, the sensor signal S(t) 66 is indicative of both respiration-related motion and respiration-related sound. This is also true for a sensor employing only an accelerometer, or for a sensor employing only a magnetometer. Accordingly, it is recognized herein that the sensor signal S(t) 66 indicative of both respiration-related motion and respiration-related sound can be decomposed into a low frequency signal indicative of respiration-related motion, and a high frequency signal indicative of respiration-related sound.

The low frequency signal indicative of respiration-related motion is suitably extracted by processing the sensor signal S(t) 66 using a first filter 70 to extract a low frequency signal $S_{low}(t)$ 72 that is indicative of respiration-related motion. For a typical human subject, frequencies of respiration-related motion typically are in a range of about 0.1 Hz to about 2 Hz. For example, about twelve breaths per minute is typical for a human adult, which corresponds to a frequency of 0.2 Hz. Frequencies of respiration-related motion may be outside of this range for some adult human subjects, for infant or elderly subjects, for animal subjects, and so forth. In one suitable embodiment of the first filter 70, The sensor signal S(t) 66 is filtered by a triangular moving average window with a width of 0.4 seconds. Other low pass or bandpass filters can also be employed. For example, the first filter 70 can also be embodied by a fast Fourier transform (FFT) and suitable spectral windowing to select frequencies of respiration-related motion.

The high frequency signal indicative of respiration-related sound is suitably extracted by processing the sensor signal S(t) 66 using a second filter 80, optionally followed by an envelope filter or envelope extractor 82, to extract a high frequency signal $S_{high}(t)$ 84 that is indicative of respiration-related sound. In some embodiments of the second filter 80, the sensor signal S(t) 66 is bandpass filtered using a Butterworth finite impulse response (FIR) filter, with about 60 Hz to 80 Hz as a lower bandpass limit and about 1000 Hz to about 1100 Hz as an upper bandpass limit. In some such embodiments, the Butterworth FIR filter has attenuation of about 60 dB in the stop bands and about 1 dB in the pass band. In other embodiments, the second filter 80 may be embodied by an FFT (optionally a same FFT used in the first filter 70) and suitable spectral windowing to select frequencies of respiration-related sound. In one suitable embodiment of the envelope filter or envelope extractor 82, the sensor signal S(t) 66 after filtering by the second filter 80 is squared and a triangular moving window with a width of 0.1 seconds is applied to extract the high frequency signal $S_{high}(t)$ 84. Other envelope filters or extractors can also be used, such as a peak detector-based envelope filter.

With continuing reference to FIG. 1 and with further reference to FIG. 3, a signals synthesizer 90 synthesizes the respiratory monitor signal 46 from the low frequency signal $S_{low}(t)$ 72 that is indicative of respiration-related motion and the high frequency signal $S_{high}(t)$ 84 that is indicative of respiration-related sound. In shallow breathing, respiration-related motion is typically detectable, but respiration-related sound may be too weak to detect. In this case, the signals synthesizer 90 suitably uses only the low frequency signal $S_{low}(t)$ 72 that is indicative of respiration-related motion as the respiratory monitor signal 46, optionally processed by selected signal processing. On the other hand, FIG. 3 illustrates the signals for heavy breathing, including: the sensor signal S(t) 66 (using an accelerometer as the sensor); the low frequency signal $S_{low}(t)$ 72 indicative of respiration-related motion; the sensor signal S(t) 66 after processing by the second filter 80; and the high frequency signal $S_{high}(t)$ 84 indicative of respiration-related sound. Here both the low frequency signal $S_{low}(t)$ 72 indicative of respiration-related motion and the high frequency signal $S_{high}(t)$ 84 indicative of respiration-related sound show periodicity indicative of respiration. Air flow causes sound at inspiration and expiration, and so the envelope of the sound signal, that is, the high frequency signal $S_{high}(t)$ 84, has respiration-related periodicity at double the frequency of the respiration-related periodicity of the low frequency signal $S_{low}(t)$ 72 indicative of respiration-related motion, as indicated by the vertical lines in FIG. 3. In the example of FIG. 3 the two signals 72, 82 are substantially in-phase; however, depending upon the detailed signal processing there may be a phase shift between these signals.

The signals synthesizer 90 can synthesize the respiratory monitor signal 46 in various ways. In some embodiments, the respiratory monitor signal 46 outputs respiratory rate values indicating the respiration period. For this approach, the low frequency signal $S_{low}(t)$ 72 and the high frequency signal $S_{high}(t)$ 84 are each suitably processed by an FFT to identify the respiration rate, and synthesis can entail averaging the two values, taking the respiration rate value derived from the stronger signal, or so forth. Another approach is to compute the cross-correlation of $S_{low}(t)$ 72 and $S_{high}(t)$ 84 and determining the periodicity of the cross-correlation.

In other embodiments, the respiratory monitor signal 46 is a continuous signal constructed by combining the low frequency signal $S_{low}(t)$ 72 and the high frequency signal $S_{high}(t)$ 84 using a cross-correlation or other combinative approach, or constructed by selecting the stronger signal over a selected time interval, or constructed by selecting the signal having the largest frequency component in the respiration range of about 0.1-2.0 Hz over a selected time interval, or so forth. In another approach, both signals $S_{low}(t)$ 72 and $S_{high}(t)$ 84 can be displayed on the display 50 of the computer 38 so that a physician or other medical person can utilize whichever of the signals 72, 82 visually provides the strongest respiration-related characteristic.

The breathing monitor user interface 48 can also include an alarm, either instead of or in addition to a visual tracking of the respiration signal or respiration rate. For example, the respiration rate can be derived from both signals 72, 82, and an alarm sounded only of both signals exhibit life-threatening characteristics (e.g., low or non-existent respiration-related characteristics).

The respiratory monitoring process 44 illustrated in FIG. 1 employs the single sensor signal S(t) 66 acquired from the single sensor 20. In other embodiments, multiple sensors 20, 22 may be used. For example, the sensor 20 may serve as input to the first filter 70 to derive the low frequency signal $S_{low}(t)$ 72 indicative of respiration-related motion, and the separate sensor 22 may serve as input to the second filter 80 to derive the high frequency signal $S_{high}(t)$ 84 indicative of respiration-related sound. In such embodiments, each sensor 20, 22 is suitably selected to effectively perform its respective task. For example, the sensor 20 may be selected as the illustrated cooperating accelerometer 30 and magnetometer 32, or may be selected as a triple-axis accelerometer (that is, three accelerometers arranged to monitor accelerations in three orthogonal spatial directions to provide orientation independence), or so forth, while the sensor 22 may be selected as a piezoelectric element configured to measure respiration-related sound.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A respiratory monitor comprising:
    a sensor configured to generate a sensor signal indicative of both respiration-related motion and respiration-related sound, the sensor including:
        a single accelerometer configured for attachment to a respiring subject and measuring an acceleration $A=G\cdot\cos(\varphi)$ where A is the acceleration measured by the accelerometer, G is the magnitude of the gravitation vector, and $\varphi$ is an orientation angle of the accelerometer,
        a magnetometer coupled with the accelerometer such that the accelerometer and the magnetometer have a common orientation; and
        a signal processor configured to generate the sensor signal based on the acceleration measured by the accelerometer and a magnetometer signal output by the magnetometer;
    a first filter configured to generate a respiration-related motion monitoring signal indicative of respiration-related motion by extracting from the sensor signal a low frequency signal encompassing frequencies of respiration-related motion;
    a second filter configured to generate a sound monitoring signal indicative of respiration-related sound by extracting from the sensor signal a high frequency signal encompassing frequencies of respiration-related sound, the respiration-related sound monitoring signal being based on the high frequency signal; and
    a signals synthesizer configured to synthesize a respiratory monitor signal by combining the respiration-related motion monitoring signal and the respiration-related sound monitoring signal to form the respiratory monitor signal.

2. The respiratory monitor as set forth in claim 1, wherein the second filter further comprises:
    an envelope filter or extractor configured to generate an envelope signal corresponding to an envelope of the high frequency signal, the respiration-related sound monitoring signal being based on the envelope signal.

3. The respiratory monitor as set forth in claim 1, wherein the accelerometer and the magnetometer are monolithically integrated on a common substrate.

4. The respiratory monitor as set forth in claim 1 wherein:
    the signals synthesizer is configured to synthesize the respiratory monitor signal by computing a cross-correlation of the respiration-related motion monitoring signal and the respiration-related sound monitoring signal.

5. A sensor for use in respiratory monitoring, the sensor comprising:
    an accelerometer;
    a magnetometer defining together with the accelerometer a unitary sensor configured for attachment to a respiring subject so as to move as a unit responsive to respiration-related motion of the respiring subject; and a signal processor configured to generate a respiratory monitor signal based on a single signal comprising change as a function of time of the angle of a three degrees of freedom (3 DOF) rotation of the unitary sensor computed from an accelerometer signal output by the accelerometer and a magnetometer signal output by the magnetometer.

6. The sensor of claim 5, wherein the signal processor is configured compute the 3 DOF rotation based on Euler angles.

7. The sensor of claim 5, wherein the signal processor is configured compute the 3 DOF rotation based on a 3×3 rotation matrix.

8. The sensor of claim 5, wherein the signal processor is configured compute the 3 DOF rotation using the axis-angle approach.

9. The sensor of claim 5, wherein the signal processor is configured compute the 3 DOF rotation using the quaternion approach.

10. A sensor for use in respiratory monitoring, the sensor comprising:

a single accelerometer measuring an acceleration $A = G \cdot \cos(\varphi)$ where A is the acceleration measured by the accelerometer, G is the magnitude of the gravitation vector, and $\varphi$ is an orientation angle of the accelerometer;

a single magnetometer defining together with the single accelerometer a unitary sensor configured for attachment to a respiring subject so as to move as a unit responsive to respiration-related motion of the respiring subject; and a signal processor configured to generate a respiratory monitor signal based on change as a function of time of the angle of a three degrees of freedom (3 DOF) rotation of the unitary sensor computed from the acceleration measured by the single accelerometer and a magnetometer signal output by the single magnetometer.

11. The sensor of claim 10, wherein the single accelerometer and the single magnetometer are monolithically integrated on a common substrate.

* * * * *